(12) United States Patent
Ricker

(10) Patent No.: US 9,744,103 B1
(45) Date of Patent: Aug. 29, 2017

(54) INFANT TEETHING APPARATUS

(71) Applicant: Chad Ricker, Jupiter, FL (US)

(72) Inventor: Chad Ricker, Jupiter, FL (US)

(*) Notice: Subject to any disclaimer, the term of this patent is extended or adjusted under 35 U.S.C. 154(b) by 573 days.

(21) Appl. No.: 14/195,465

(22) Filed: Mar. 3, 2014

Related U.S. Application Data

(60) Provisional application No. 61/851,422, filed on Mar. 8, 2013.

(51) Int. Cl.
A61J 17/02 (2006.01)

(52) U.S. Cl.
CPC .................. A61J 17/02 (2013.01)

(58) Field of Classification Search
CPC   A61J 19/00; A61J 17/02; A61J 17/007; A61J 17/001; A63H 3/00; A63H 1/00; A01K 15/025; A01K 15/026; A41B 13/00; A41B 13/10; A41B 13/106; A45C 1/02; A45C 1/08; A44C 3/00; A44C 5/00; A44C 11/00; A44C 25/00; A44B 6/00; A44B 11/00
See application file for complete search history.

(56) References Cited

U.S. PATENT DOCUMENTS 5,993,478 A * 11/1999 Nowak .................. A61J 17/02 606/234
2002/0026670 A1 * 3/2002 Dunn .................... A61J 17/007 5/482

* cited by examiner

Primary Examiner — Tuan V Nguyen
Assistant Examiner — Chima Igboko
(74) Attorney, Agent, or Firm — Glenn E. Gold, P.A.; Glenn E. Gold

(57) ABSTRACT

A generally triangular teething apparatus incorporating slots is provided for receiving and securing a cleaning cloth. The teething apparatus includes a body portion having a teething portion, a cross-bar and a rear bar. A first slot is defined between the teething portion and the cross-bar while a second slot is defined between the cross-bar and the rear bar. The rear bar includes a top flexible bar or flap and a bottom flexible bar or flat that define a third slot therebetween and oriented transverse to the second slot. The teething portion is provided with a series of bumps for therapeutic purposes. There is also method of attaching a cleaning cloth to the teething apparatus by threading the cleaning cloth through the slots.

18 Claims, 4 Drawing Sheets

INFANT TEETHING APPARATUS

CROSS-REFERENCE TO RELATED APPLICATIONS

This U.S. non-provisional patent application claims the benefit of U.S. provisional patent application No. 61/851,422, filed on Mar. 8, 2013, the entire contents of which are incorporated by reference herein.

FIELD OF THE INVENTION

The present invention relates to an infant teething apparatus and method of use, and more particularly, to an infant teething apparatus having a construction enabling and facilitating releasable attachment of a burping or cleaning cloth thereto.

BACKGROUND OF THE INVENTION

During the early stages of a baby's or child's development, there is an instinctual need to suckle and chew. These instincts encourage feeding and working the child's baby teeth and gums to promote healthy development. Many teething type devices are available to a parent to provide the child with something to suck and chew on while not actually feeding. These devices typically include a soft body that is placed in the child's mouth while under the supervision of the parent.

A byproduct of the child chewing sucking on the teething device is the production of saliva or "drool" which escapes from the child's mouth and onto their clothing. Often the child is held by the parent or another while using the teething device resulting in the drool running onto the parents clothing as well. Additionally, other fluids or matter such as mucus, blood, fluid or solid food particles may escape the child's mouth and fall onto the clothing.

Typically, parents carry an absorbent material such as a cloth over their arm or shoulder when holding the child during teething or feeding. This allows the parent to burp or otherwise rock the child without fear of getting fluids onto their clothing. This presents its own problems, however, in that the cloth may slip off the parent and may require two hands to deal with the teething device and separate cloth, as well as holding the child.

Accordingly, there remains a need in the art for a teething device capable of receiving and securing a separate cleaning cloth to facilitate use of both by the parent.

SUMMARY OF THE INVENTION

The present invention overcomes the deficiencies of the known art and the problems that remain unsolved by providing an apparatus and method for attaching a cleaning cloth to the teething apparatus.

In accordance with one implementation of the invention, a teething apparatus is provided comprising:

a body portion having an upper surface, a lower surface, a front edge and a rear edge;

the body portion defining a first slot extending through the body portion from the upper surface to the lower surface, a second slot extending through the body portion from the upper surface to the lower surface; and a third slot extending into the body portion and the second slot.

In second aspect, the third slot is oriented transverse to the second slot.

In another aspect, the body portion includes a cross-bar separating the first slot from the second slot.

In another aspect, the cross-bar has a polygonal cross-section.

In another aspect, the cross-bar has at least one angled side.

In another aspect, the angled side of the cross-bar terminates in a generally sharp edge.

In another aspect, the body portion further includes a rear bar defining the third slot.

In another aspect, the rear bar includes at least one flexible flap.

In another aspect, the rear bar includes a first flexible flap and a second flexible flap, the first and second flexible flaps defining the third slot therebetween.

In another aspect, the body portion is formed from a bio-compatible material.

In another aspect, the at least one of the upper and lower surfaces includes therapeutic bumps.

In a further implementation, a teething apparatus is provided comprising:

a generally triangular body portion having an upper surface, a lower surface, an arcuate front edge, an arcuate rear edge, a first side extending from the arcuate front edge to the arcuate rear edge and a second side extending from the arcuate front edge to the arcuate rear edge;

a teething portion adjacent to the arcuate front edge;

a cross-bar; and a rear bar, the cross-bar being located between the teething portion and the rear bar.

In another aspect, the teething portion and the cross-bar define a first slot therebetween.

In another aspect, the cross-bar and the rear bar define a second slot therebetween.

In another aspect, the rear bar defines a third slot therethrough, the third slot being oriented transverse to the second slot.

In another aspect, the third bar includes a top flexible flap and a bottom flexible flap, the top and bottom flexible flaps defining the third slot therebetween.

In another aspect, the teething portion includes bumps formed on at least one of the upper and lower surfaces.

In another aspect, the teething portion includes small bumps and large bumps formed on at least one of the upper and lower surfaces.

Introducing another embodiment, there is a method of releasably securing a cloth to a teething apparatus, said method comprises:

providing a teething apparatus having body portion including an upper surface, a lower surface and a rear edge, said body portion including a teething portion, a cross-bar and a rear bar, a first slot defined between said teething portion and said cross-bar, a second slot defined between said cross-bar and said rear bar;

inserting a leading edge of a cleaning cloth through said second slot toward said upper surface and over a portion of said cross-bar;

advancing the leading edge through the first slot from the upper surface toward said lower surface and around the cross-bar; and moving the leading edge back into a portion of the second slot.

In another aspect, the method further comprises a step of:
providing a third slot extending through the rear bar and oriented transverse to said second slot;

prior to the step of inserting, positioning said leading edge of said cloth through said third slot in a first direction; and after the step of moving, pulling said leading edge of said cloth through said third slot in a second direction opposite of that of said first direction.

These and other aspects, features, and advantages of the present invention will become more readily apparent from the attached drawings and the detailed description of the exemplary implementations, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
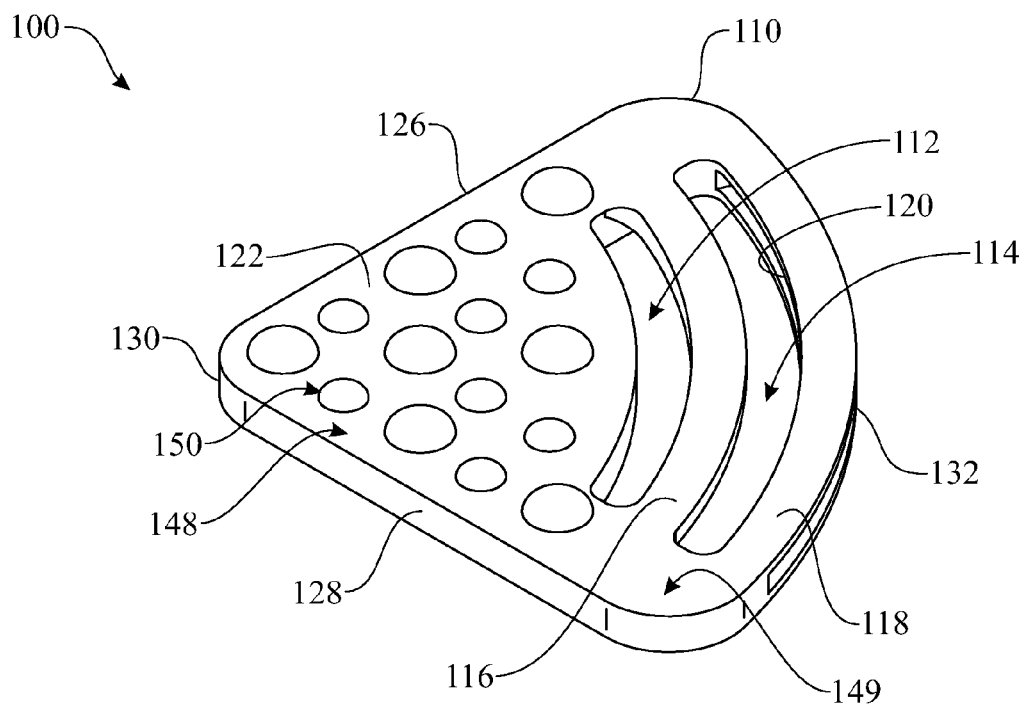
FIG. 1 presents an isometric, top view of an exemplary infant teething apparatus.
Figure 2:
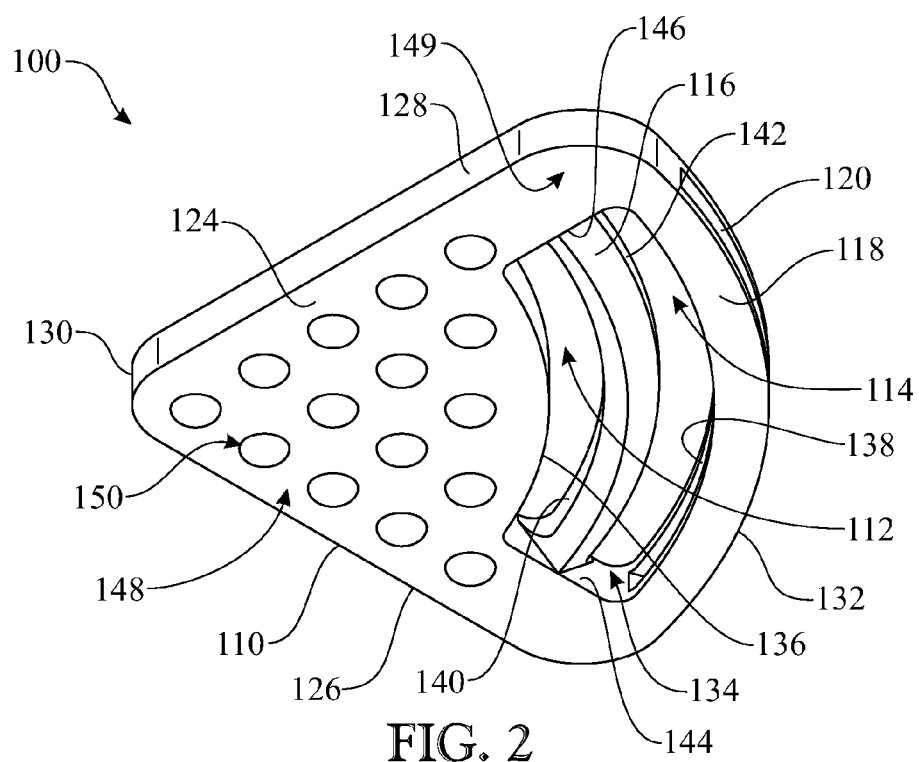
FIG. 2 presents an isometric bottom view of the infant teething apparatus.

An infant teething and buckle apparatus 100 and method of use is presented in various orientations in the illustrations of FIGS. 1 through 7. Referring initially to FIGS. 1 and 2, the infant teething apparatus 100 is provided to pacify a child during a teething time in its early life and provide a point of attachment for a burping or cleaning cloth 200 (FIG. 5), described in more detail herein below. Attaching the cleaning cloth 200 directly to the teething apparatus 100 allows a parent to conveniently burp or otherwise hold and keep clean a child during the teething phase of its life. The infant teething apparatus 100 generally includes a body portion 110 having spaced apart upper and lower surfaces 122 and 124 disposed in a generally parallel relationship to one another, and a periphery surrounding the body portion and extending between and interconnecting the upper and lower surfaces. The body portion 110 also has teething and buckle sections 148, 149 disposed in a tandem relationship to one another and surrounded by the periphery of the body portion. The buckle section 149 defines a first slot 112, a second slot 114 and a third slot 120, being configured for receipt and securement of a portion of the cleaning cloth 200 to the buckle section 149. The first slot 112 extends through the body portion 110 from the upper surface 122 to the lower surface 124 and is disposed adjacent to the teething section 148 of the body portion. The second slot 114 is spaced from the first slot 112 and extends through the body portion 110 from the upper surface 122 to the lower surface 124. The third slot 120 extends through the body portion 110 between and spaced from the upper and lower surfaces 122 and 124 of the body portion. The third slot 120 opens into the second slot 114 and also opens at an exterior location on the periphery of the body portion spaced from the second slot.

The buckle portion 149 of the body portion 110 of the teething apparatus 100 also includes a cross-bar 116 formed in the body portion, being located between and thus separating the first and second slots 112 and 114, and a rear or end bar 118 formed in the body portion, being spaced from the cross-bar 116 and defining the second slot 114 therebetween. The rear bar 118 also defines the third slot 120 oriented transverse to the second slot 114 for receipt of a portion of the cleaning cloth 200. As shown in FIGS. 1 and 2, in addition to the upper and lower surfaces 122 and 124, the body portion includes a first side edge 126 and a second side edge 128 spaced from the first side edge. In order to prevent injury to the child and provided for easier teething, the body portion 110 is generally triangular shaped and has an arcuate front edge or nose 130 interconnecting the first and second side edges 126 and 128 at the front of the body portion 110, and an arcuate rear edge 132 spaced from the arcuate front edge or nose 130 and interconnecting the first and second side edges 126 and 128 at the rear of the body portion. The periphery surrounding the body portion 110 is defined by the arcuate front edge or nose 130 and arcuate rear edge 132 interconnected by the first and second side edges 126, 128.

As best shown in FIG. 2, due to their configurations the first and second slots 112 and 114 converge with one another so as to form an opening 134 in the lower surface 124 of the body portion 110. This allows a portion of the cleaning cloth 200 to more easily wrap around the cross-bar 116. The first and second slots 112 and 114 extend from the upper surface 122, through body portion 110 and open out at the lower opening 134. The lower opening 134 of the first and second slots 112 and 114 is defined by a first inner arcuate edge 136 formed in the body portion 110 and a second inner arcuate edge 138 on rear bar 118. It should be noted that, the cross-bar 116 includes third and fourth inner arcuate edges 140 and 142. The lower opening 134 is further defined by first and second side inner edges 144 and 146 formed in the body portion 110.

With reference for the moment to both FIGS. 1 and 2, the area of the body portion 110 of the teething apparatus 100 forward of the first slot 112 forms the teething section 148 of the teething apparatus 100. This teething section 148 is provided for teething by a child and includes raised structures or bumps 150, formed in spaced apart relationship on the upper and lower surfaces 122 and 124 of the body portion 110, to sooth a child's gums and/or teeth during teething. The bumps 150 also provide a frictional surface or place for the child's teeth to grip the teething apparatus 100. While not specifically shown, the bumps 150 may also be formed on the first and second side edges 126 and 128, as well as on the arcuate front edge 130.

The body portion 110 is formed from a medical or food grade silicone or similar sufficiently safe and strong material, such as, for example, a BFA free plastic. Further, the body portion 110 may be integrally formed or the various sections may be formed separately from same or similar materials. The material of the body portion may be colored to enhance the pleasure of the child or otherwise marked with symbols, figures or indicia for the pleasure of the child and/or to facilitate handling and identification of the parent or user.

Figure 3:
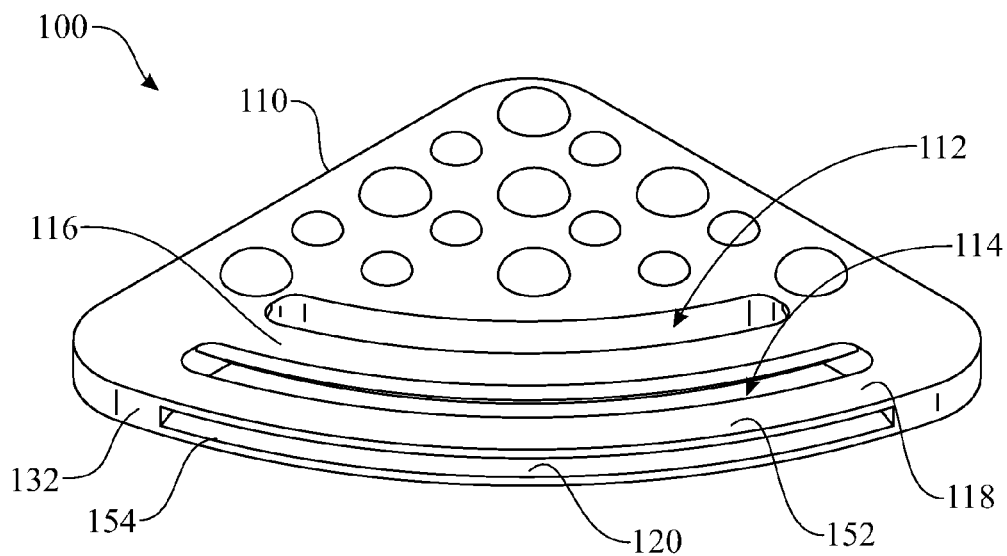
FIG. 3 presents a front, perspective view of the infant teething apparatus.

Referring now to FIG. 3, the third slot 120 is defined within the rear bar 118. Specifically, the rear bar 118 includes a first, top flexible bar or flap 152 and a second, bottom flexible bar or flap 154. The top flexible flap 152 and bottom flexible flap 154 are specifically designed to flex or splay open to more easily insert a section of the burping or cleaning cloth 200 therebetween.

Figure 4:
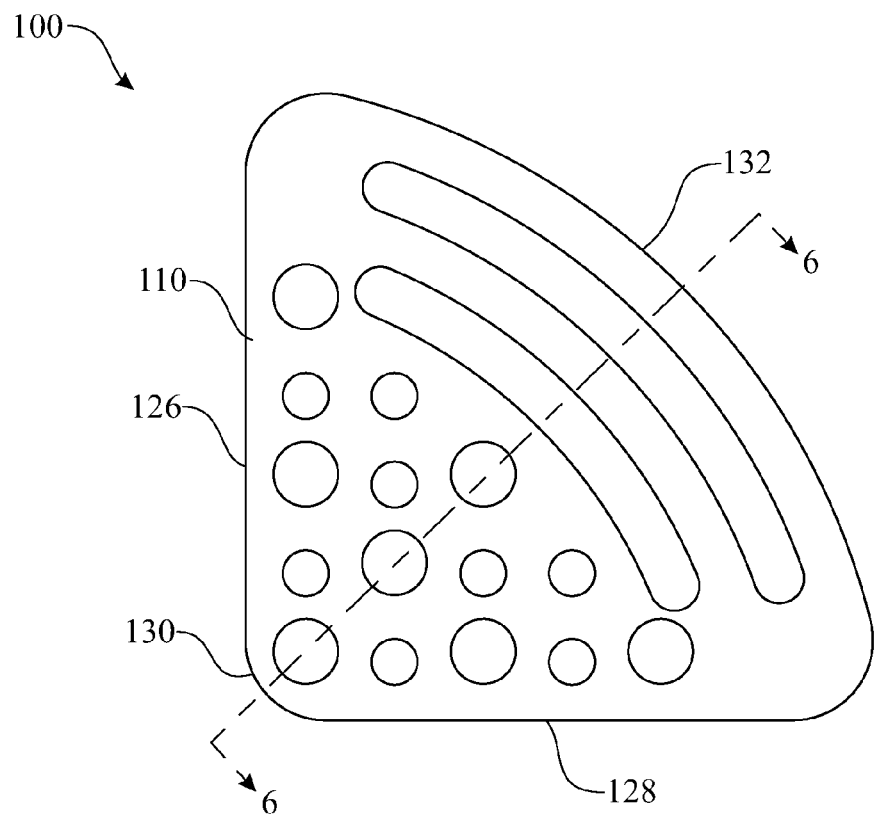
FIG. 4 presents a top view of the infant teething apparatus.

As specifically shown in FIG. 4, the body portion 110 of the teething apparatus 100 is formed in a generally rounded off, atraumatic triangular shape. It is contemplated that the teething apparatus 100 incorporating the disclosed "buckle" type cloth retention structure may be formed with various other atraumatic symmetrical or asymmetrical shapes such as, for example, round, generally rectangular, kidney shaped, oval, etc. This may be of particular advantage when it is desired to target and treat specific areas of a child's mouth during teething for therapeutic, orthodontic or other medical reason.

Figure 5:
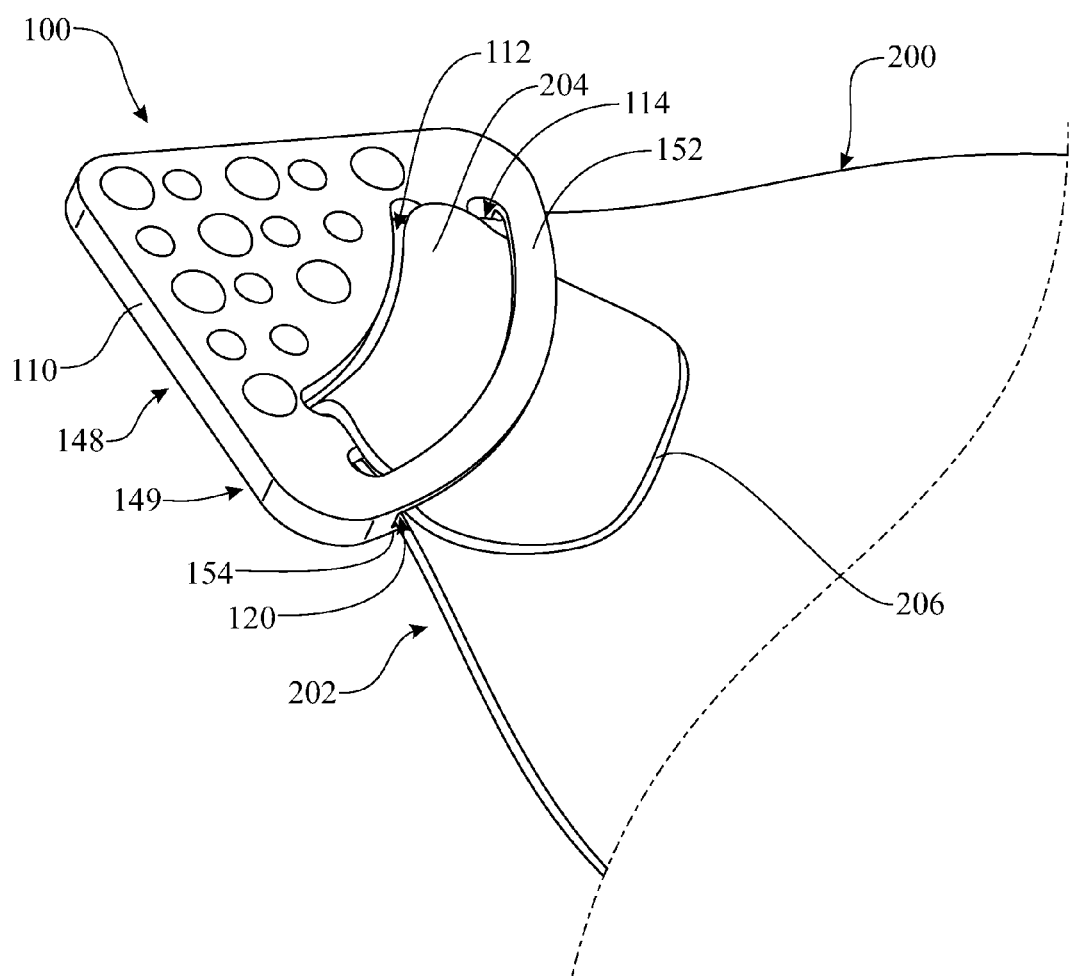
FIG. 5 presents an isometric view of the infant teething apparatus, originally introduced in FIG. 1, with an attached section of cloth.
Figure 6:
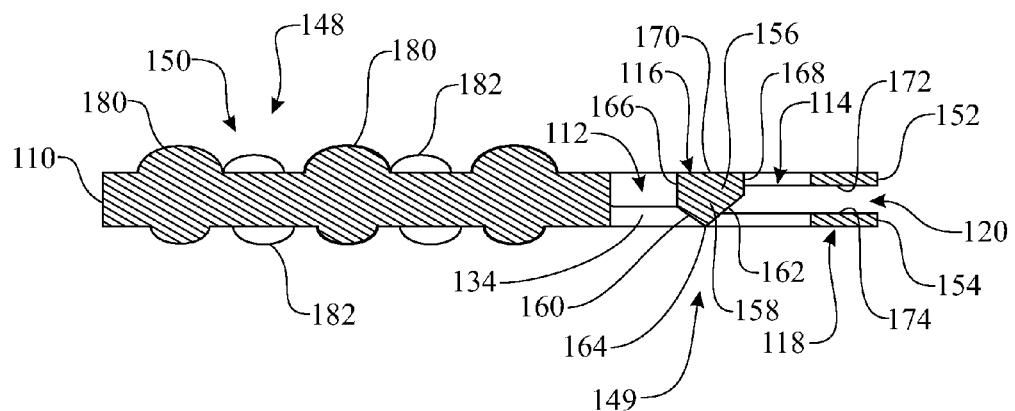
FIG. 6 presents a cross-sectional view, taken along line 6-6 of FIG. 4, of the infant teething apparatus.
Figure 7:
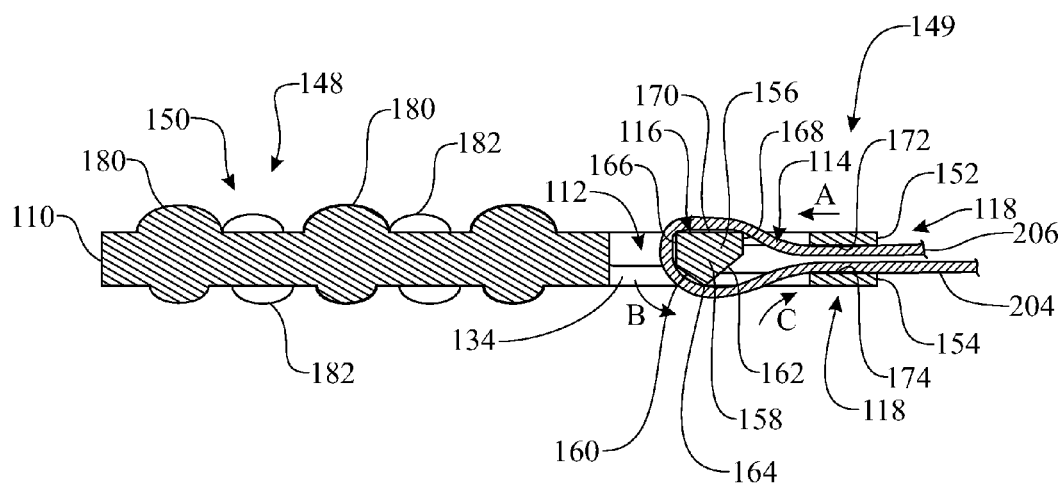
FIG. 7 presents a cross-sectional view, similar to FIG. 6, of the infant teething apparatus showing the section of cloth attached to the infant teething apparatus.

Referring now to FIGS. 5-7, and initially with regard to FIG. 5, the use of the teething apparatus 100 to receive and retain a burping or cleaning cloth, such as the cleaning cloth 200, will now be described. The cleaning cloth 200 is formed from a child safe material, such as cotton, and is provided to absorb blood, mucus, drool, juices or food particles, exiting a child's mouth or nose while holding the child. It should be noted that the teething apparatus 100 is not intended to be used or left alone with the child when unattended. FIG. 5 illustrates a corner 202 of the burping cloth 200 inserted through the third slot 120, the second slot 114, the first slot 112 and back out the third slot 120.

With reference for the moment to FIG. 6, in order to more securely retain the cleaning cloth 200 within the teething apparatus 100, the cross-bar 116, located between the first and second slots 112 and 114, has a polygonal cross-section 156 including a downward facing triangular bottom portion 158 pointing away from the first and second slots 112 and 114. The triangular bottom portion 158 includes a first angled side 160 and a second angled side 162 which converge to form a transverse or relatively sharp cross edge 164 that intersects the lower opening 134. As shown, sharp cross edge 164 is "tucked up" within the fourth opening 134 and poses no danger to a child. Alternatively, the sharp cross edge 164 may be slightly rounded off to form a bluntly sharpened edge, etc. The relatively sharp edge 164 assists in retaining the cleaning cloth 200 within the body portion 110. The remainder of the cross-bar 116 includes a forward flat side 166, a rearward flat side 168 and a flat top surface 170 generally flush with upper surface 122 of the body portion 110.

Referring now to FIGS. 5 and 7, in order to secure the cleaning cloth 200 to the teething apparatus 100, a length of material 204 on corner 202 of cleaning cloth 200 is inserted along a path, as defined by arrows A-C in FIG. 7, that advances through the third slot 120 in the first direction of arrow "A", therefrom into the second slot 114 and over the cross-bar 116 into the first slot 112, and then back around the cross-bar 116 in the direction of arrow "B" along the lower opening 134 and finally back out the third slot 120 in the second direction of arrow "C" being opposite to the first direction of arrow "A". Thus, the path defined by the first, second and third slots 112, 114 and 120, together with the cross-bar 116 and the rear bar 118, is in the shape of a loop through the first and second slots and past the cross-bar that doubles back upon itself within the third slot so as to configure the buckle section 149 to receive and releasably secure the cleaning cloth to the buckle section of the body portion 110 of the teething apparatus 100.

With specific reference to FIG. 7, a leading edge 206 of the length of material 204 on the corner 200 of the burping cloth 200 is initially inserted through the third slot 120 of the teething apparatus 100 and drawn upward against a lower surface 172 of the top flexible flap 252. The leading edge 206 is then passed upward through the second slot 114 and over the flat top surface 170 of the cross-bar 116. The leading edge 206 of the length of material 204 is then inserted down through the first slot 112 and along and around the forward flat side 166 of the cross-bar 116 and out through the fourth opening 134. The leading edge 206 continues to be passed along the first angled side 162, over the cross edge 164 and back up into the second slot 114. To finish attaching the cleaning cloth 200 the teething apparatus 100, the leading edge 206 is then again passed through the third slot 120 up and over an upper surface 174 of the bottom flexible flap 154 and out of the rear bar 118 of the teething apparatus.

The top and bottom flexible flaps 152 and 154 allow the relatively thick length of material 204 of the cleaning cloth 200 to more easily pass through the third slot 120 and assist in retaining the cleaning cloth 200 by pinching the length of material 204 therebetween. More importantly, the passage of the length of material 204 through the second and first slots 114 and 112, respectively, and around the polygonal cross-section 170 of the cross-bar 116 wedged and secures the length of material 204 within the body portion 110 of the teething apparatus 100 in "buckle" type fashion.

Additionally, the teething apparatus 100 serves as a hand hold for a used cleaning cloth 200 as well as a weight which assists in maintaining the assembled teething apparatus 100 and cleaning cloth 200 on the user arm or shoulder. Specifically, the teething apparatus 100 acts as a counterweight when the combined cleaning cloth 200 and teething apparatus 100 are thrown or draped over a user's arm or shoulder to prevent dropping them and contaminating them with dirt, etc.

In order to remove the cleaning cloth 200 from the teething apparatus 100, the length of material 204 is pushed slightly into the third slot 120 flexing the top and bottom flexible flaps 152 and 154 such that the leading edge 206 of the length of material is free to be pulled back around the cross-bar 116 and out of the third slot 120.

Referring for the moment to FIGS. 6 and 7, as noted hereinabove, the body portion 110 of the teething apparatus includes therapeutic bumps 150 formed on the teething section 148 of the teething apparatus 100. The bumps 150 may be formed symmetrically (as shown) across the upper and lower surfaces 122 and 124 of the body portion 110 or may be spaced asymmetrically or randomly across the upper and lower surfaces 122 and 124. Additionally, the bumps 150 may consist of bumps of differing shapes or sizes such as, for example, large bumps 180 and small bumps 182. Still further the bumps 150 may be solid as shown or may be hollow or otherwise more flexible than the body portion 110 itself, to increase any therapeutic action within a child's mouth.

In this manner, the teething apparatus 100 provides a novel and useful device for retaining the cleaning cloth 200 while burping or cleaning a child.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A teething apparatus comprising:
    a body portion having an upper surface, a lower surface spaced from said upper surface, and a periphery surrounding said body portion and extending between and interconnecting said upper and lower surfaces;
    said body portion comprising a teething section and a buckle section in a tandem relationship with one another, said buckle section defining
        a first slot extending through said body portion from said upper surface to said lower surface of said body portion, and being disposed adjacent to said teething section of said body portion,
        a second slot spaced from said first slot and extending through said body portion from said upper surface to said lower surface of said body portion,
        a cross-bar formed in said body portion disposed between said first and second slots so as to separate said first slot from said second slot, and
        a third slot extending through said body portion between and spaced from said upper and lower surfaces of said body portion, said third slot opening into said second slot and also opening at an exterior location on said periphery of said body portion spaced from said second slot;
    wherein said first, second and third slots, together with said cross-bar, of said buckle section define a path in the shape of a loop through said first and second slots and past said cross-bar that doubles back upon itself within said third slot so as to configure said buckle section to receive and releasably secure a cleaning cloth to said buckle section of said body portion by inserting a portion of the cleaning cloth from adjacent to said exterior location on said periphery of said body portion along said path in a first direction through said third slot and into said second slot, further along said path about a portion of said cross-bar and through said first slot, still further along said path back into said second slot, and lastly along said path back from said second slot and in a second direction, opposite to said first direction, through said third slot to adjacent said exterior location on said periphery of said body portion.

2. The teething apparatus as recited in claim 1, wherein said third slot is oriented transverse to said second slot.

3. The teething apparatus as recited in claim 1, wherein said buckle section of said body portion also defines an end bar formed in said body portion extending along a portion of said periphery of said body portion and being spaced from said cross-bar so as to define said second slot between said end bar and said cross-bar, said end bar also defining said third slot oriented transverse to said second slot.

4. The teething apparatus as recited in claim 3, wherein said end bar includes at least one flexible flap.

5. The teething apparatus as recited in claim 3, wherein said end bar includes a first flexible flap and a second flexible flap, said first and second flexible flaps define said third slot.

6. The teething apparatus as recited in claim 1, wherein said cross-bar has a polygonal cross-section with a triangular portion pointing away from said first and second slots.

7. The teething apparatus as recited in claim 6, wherein said triangular portion of said cross-bar terminates in a generally sharp edge that assists in retaining the portion of the cleaning cloth inserted in said path defined by said first, second and third slots and about said cross-bar of said body portion.

8. The teething apparatus as recited in claim 1, wherein said body portion is formed from a bio-compatible material.

9. The teething apparatus as recited in claim 1, wherein at least one of said upper and lower surfaces of said body portion at said teething section thereof includes therapeutic bumps thereon.

10. A teething apparatus, comprising:
    a body portion of a generally triangular shape and having an upper surface, a lower surface spaced from said upper surface, and a periphery surrounding said body portion and extending between and interconnecting said upper and lower surfaces, said periphery being defined by an arcuate front edge, an arcuate rear edge spaced from said arcuate front edge, a first side edge extending from and interconnecting said arcuate front edge to said arcuate rear edge and a second side edge spaced from said first side edge and extending from and interconnecting said arcuate front edge to said arcuate rear edge;
    said body portion comprising a teething section and a buckle section in a tandem relationship with one another, said teething section being adjacent to said arcuate front edge of said periphery of said body portion, said buckle section being adjacent to said arcuate rear edge of said periphery of said body portion;
    said buckle section including a rear bar formed in said body portion along said arcuate rear edge of said periphery of said body portion, and a cross-bar formed in said body portion and located between said teething section and said rear bar;
    said teething section and said cross-bar defining a first slot therebetween extending through said body portion from said upper surface to said lower surface of said body portion;
    said cross-bar and said rear bar defining a second slot therebetween extending through said body portion from said upper surface to said lower surface of said body portion;

said rear bar defining a third slot through said rear bar between and spaced from said upper and lower surfaces of said body portion, said third slot opening into said second slot and also opening at an exterior location on said arcuate rear edge of said periphery of said body portion spaced from said second slot;

wherein said first, second and third slots, together with said cross-bar and rear bar, of said buckle section define a path in the shape of a loop through said first and second slots and past said cross-bar that doubles back upon itself within said third slot so as to configure said buckle section to receive and releasably secure a cleaning cloth to said buckle section of said body portion by inserting a portion of the cleaning cloth from adjacent to said exterior location on said periphery of said body portion along said path in a first direction through said third slot of said rear bar and into said second slot, further along said path about a portion of said cross-bar and through said first slot, still further along said path back into said second slot, and lastly along said path back from said second slot and in a second direction, opposite to said first direction, through said third slot of said rear bar to adjacent said exterior location on said periphery of said body portion.

11. The teething apparatus as recited in claim 10, wherein said third slot is oriented transverse to said second slot.

12. The teething apparatus as recited in claim 10, wherein said rear bar includes a top flexible flap and a bottom flexible flap, said top and bottom flexible flaps defining said third slot therebetween.

13. The teething apparatus as recited in claim, 12, wherein said teething section includes bumps formed on at least one of said upper and lower surfaces.

14. The teething apparatus as recited in claim 13, wherein said bumps of said teething section are of small and large sizes relative to one another.

15. A method of releasably securing a cleaning cloth to a teething apparatus, said method comprising:
  obtaining a teething apparatus having a body portion including an upper surface, a lower surface spaced from said upper surface, and a periphery surrounding said body portion and extending between and interconnecting said upper and lower surfaces, said body portion also including a teething section and a buckle section in a tandem relationship with one another, said buckle section defining a cross-bar formed in said body portion, an end bar formed in said body portion being spaced from said cross-bar, a first slot between said teething section and said cross-bar extending through said body portion from said upper surface to said lower surface of said body portion, a second slot between said cross-bar and said end bar extending through said body portion from said upper surface to said lower surface of said body portion, and a third slot extending through said end bar between and spaced from said upper and lower surfaces of said body portion and oriented transverse to said second slot, said third slot opening into said second slot and also opening at an exterior location on said periphery of said body portion spaced from said second slot, wherein said first, second and third slots, together with said cross-bar and end bar, of said buckle section define a path in the shape of a loop through said first and second slots and past said cross-bar that doubles back upon itself within said third slot so as to configure said buckle section to receive and releasably secure a cleaning cloth to said buckle section of said body portion; and releasably securing a cleaning cloth to said buckle section of said body portion by
    inserting a portion of a cleaning cloth from adjacent to said exterior location on said periphery of said body portion along said path through said third slot of said end bar and into said second slot,
    next advancing the portion of the cleaning cloth further along said path about a portion of said cross-bar and through said first slot,
    then advancing the portion of the cleaning cloth still further along said path back into said second slot, and
    moving the portion of the cleaning cloth from said second slot yet further along said path back through said third slot of said end bar to adjacent said exterior location on said periphery of said body portion.

16. The method as recited in claim 15, wherein
  said inserting the portion of the cleaning cloth from adjacent to said exterior location on said periphery of said body portion through said third slot of said end bar and into said second slot occurs in a first direction; and
  said moving the portion of the cleaning cloth from said second slot back through said third slot of said end bar occurs in a second direction opposite of that of said first direction.

17. The method as recited in claim 15, wherein the portion of the cleaning cloth is advanced along said path through a portion of said second slot toward said upper surface of said body portion and over said cross-bar prior to being advanced about a portion of said cross-bar and through said first slot.

18. The method as recited in claim 17, wherein the portion of the cleaning cloth is advanced along said path past said cross-bar and through said first slot from said upper surface toward said lower surface and around said cross-bar prior to being advanced along said path back into another portion of said second slot.

* * * * *